United States Patent [19]

Lionelle et al.

[11] 4,347,321

[45] Aug. 31, 1982

[54] METHOD AND APPARATUS FOR PRODUCING ALCOHOL

[75] Inventors: Joseph E. Lionelle; Jeffrey A. Staffa; William L. McCormick, all of Salida, Colo.

[73] Assignee: Bio-Systems Research, Inc., Salida, Colo.

[21] Appl. No.: 194,850

[22] Filed: Oct. 7, 1980

[51] Int. Cl.³ .......................... B01D 3/14; C12M 1/02; C12P 7/06

[52] U.S. Cl. .................................... 435/161; 435/302; 435/316; 122/441; 202/154; 202/186; 202/198; 202/175; 203/19; 203/87; 203/DIG. 6; 203/DIG. 13; 203/DIG. 16; 203/82; 426/494

[58] Field of Search ....................... 203/87, 19, 73, 74, 203/81, 82, DIG. 13, DIG. 16, DIG. 6, 25; 202/186, 198, 179, 154, 175, 166, 167; 435/161–165, 316, 302; 426/14, 493, 494; 126/361; 196/123–125; 159/6, 16, 25; 122/441, 442

[56] References Cited

U.S. PATENT DOCUMENTS

| | | | |
|---|---|---|---|
| 63,116 | 3/1867 | Tait et al. | 435/161 |
| 67,863 | 8/1867 | Foubert | 202/198 |
| 102,633 | 5/1870 | Wheeler et al. | 435/161 |
| 858,346 | 6/1907 | Llodra | 202/186 |
| 1,466,221 | 8/1923 | Foster et al. | 202/198 |
| 1,509,634 | 9/1924 | Brown | 203/DIG. 17 |
| 2,053,769 | 9/1936 | Dreyfus | 435/161 |
| 2,438,252 | 3/1948 | Richardson | 203/87 |
| 2,802,774 | 8/1957 | Griesbach | 435/161 |
| 3,864,214 | 2/1975 | Ohakas | 202/186 |
| 4,009,075 | 2/1977 | Hoge | 435/165 |

OTHER PUBLICATIONS

Carley, L. W.: *How to Make Your Own Alcohol Fuels;* Aug. 1980, pp. 28–33, 64–67, 76–81.

*Primary Examiner*—Wilbur L. Bascomb, Jr.
*Attorney, Agent, or Firm*—Larson and Taylor

[57] ABSTRACT

A method and apparatus particularly suitable for the production of alcohol from fermentable substances such as grain. In this method, mash cooking, fermentation, and boiling are carried out sequentially in a single vessel. Boiling produces a first vapor rich in alcohol which is partially condensed to form a liquid condensate and a second vapor which is further enriched in alcohol. The liquid condensate is returned to the vessel and an alcohol product is recovered from the second vapor, preferably without the addition of external heat. Alcohol recovery is effected by passing the second vapor to a second vessel. Vapor from the second vessel is partially condensed to form a third vapor which is still further enriched in alcohol and a liquid condensate which is returned to the second vessel where it is contacted by the second vapor introduced thereto. The apparatus comprises a single vessel for effecting the heating, boiling and fermenting steps and is provided with heating and cooling means for establishing appropriate temperatures for these steps. Partial condensation is achieved in packed columns having cooling means in the upper regions thereof.

20 Claims, 1 Drawing Figure

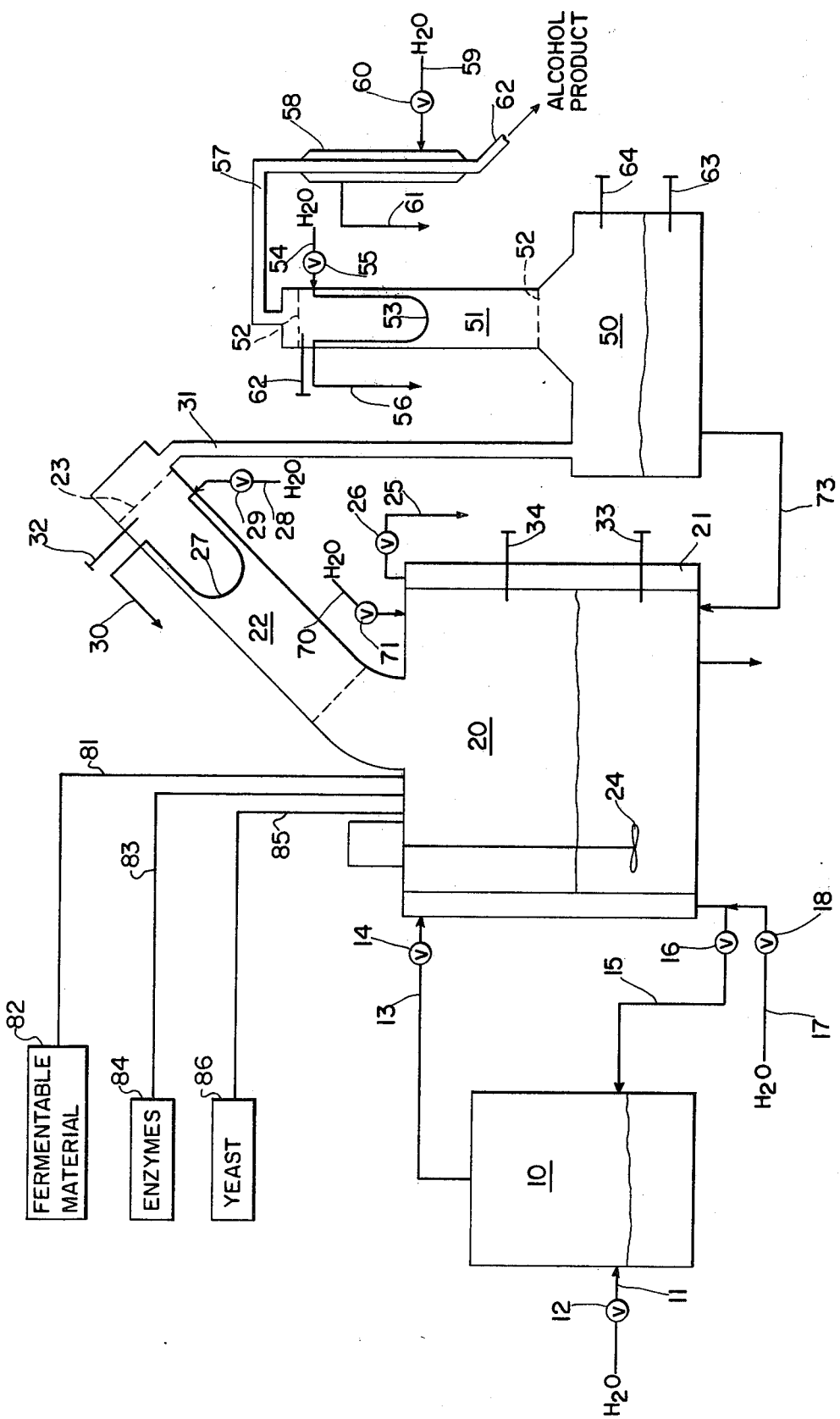

METHOD AND APPARATUS FOR PRODUCING ALCOHOL

BACKGROUND OF THE INVENTION

This invention relates to a method and apparatus for producing alcohol from a fermentable substance. By the term "alcohol" is meant ethanol.

There has been a great deal of emphasis in the past several years on the development of new fuels for automobiles, farm machinery, and the like as full or partial substitutes for fuels derived from petroleum. One such fuel which has received considerable attention is alcohol, either as such or in admixture with other fuels, such as "gasohol". Fermentation processes for producing alcohol are attractive because of their low cost. Moreover, such processes are particularly suited for farm use because of the ready availability of low cost fermentable materials, such as grain. While several fermentation systems for producing alcohol from grain are well known, and while several others have been proposed, a system has now been developed which is very efficient, easy to operate, durable, and yet relatively inexpensive due to its simplicity and compact design.

It is an object of the present invention to provide a method and apparatus for the production of alcohol from fermentable substances. It is a further object to provide such method which is efficient and easy to carry out. It is a further object to provide such apparatus which is easy to operate and durable.

BRIEF SUMMARY OF THE INVENTION

The foregoing and other objects which will be apparent to those having ordinary skill in the art are achieved in accordance with the present invention by providing a method of producing alcohol from a fermentable material which comprises the steps of: heating a mixture of water and a fermentable material to form a cooked mash; fermenting the cooked mash to form a beer; boiling the beer to produce a first vapor rich in alcohol; partially condensing the first vapor to produce a liquid condensate and a alcohol product from said second vapor. In accordance with the invention, the steps of heating, fermenting, and boiling are carried out sequentially in a single vessel, and the liquid condensate is returned to said vessel.

Apparatus in accordance with the invention comprises: a vessel for sequentially heating a mixture of water and fermentable material to form a cooked mash, for fermenting the cooked mash to form a beer, and for boiling the beer to produce a first vapor rich in alcohol; means for supplying fermentable material to said vessel; means for supplying water to said vessel; means for heating said vessel to a temperature sufficient for forming a cooked mash and for boiling beer; means for cooling said vessel to a temperature suitable for fermentation of a cooked mash; means for supplying enzymes to said vessel; means for supplying yeast to said vessel; means for partially condensing said first vapor to produce a liquid condensate and a second vapor further enriched in alcohol; means for returning said liquid condensate to said vessel; and means for recovering an alcohol product from said second vapor.

DETAILED DESCRIPTION OF PREFERRED EMBODIMENTS

There follows a description of preferred embodiments of the invention including the drawing which is a diagrammatic sectional side elevation view of apparatus in accordance with the invention.

As shown in the drawing, apparatus according to the invention in general comprises a steam boiler 10, a mash cooking, fermentation, and beer boiling vessel 20, and a stripping vessel 50. Steam boiler 10 is a conventional design and is fired by any convenient fuel such as gas, wood, coal, etc. Water is supplied to the boiler through pipe 11 under the control of valve 12.

Vessel 20 is a stainless steel tank having a capacity of, preferably, 50 to 500 gallons. A steam heating or water cooling jacket 21 is provided on the outer periphery of the vessel. A stainless steel stripping column 22, packed with ½ inch to 1 inch diameter procelain marbles or packing saddles, is mounted with its lower end on the top of vessel 20 such that vapor from vessel 20 will pass upwardly into column 22. Column 22 extends generally upwardly and is preferably inclined at an angle of 35° to 65° from the vertical. Screens 23 are provided to contain the porcelain balls or saddles. An agitator 24 is provided to agitate the contents of vessel 20.

Vessel 20 is used to perform three separate and distinct functions: mash cooking, fermentation, and beer boiling. The cooking and boiling functions require heat and steam heat is preferably utilized as shown in the drawing. Water is supplied to boiler 10 through conduit 11 and make up water is added, as required, by valve 12 which may be automatic or manual. Steam raised in the boiler flows to jacket 21 through conduit 13 and valve 14. Condensed steam is returned to boiler 10 from jacket 21 through conduit 15 and valve 16. The boiler is conventional and the design may be shell and tube or the like. While it is preferred to use steam to heat vessel 20, it will be apparent that other types of heating may be used, both direct and indirect. For example, a heating fluid other than steam may be used and the conduit through which the steam or other heating fluid passes may be a coil located within vessel 20.

When vessel 20 is used for fermentation, much cooler temperatures, generally 60°–90° F., will prevail in vessel 20 and cooling is provided to cool the vessel contents to, and maintain the vessel contents at, a proper temperature for fermentation. In the preferred embodiment shown, cooling is provided by introducing water from a suitable source through conduit 17 and valve 18 into jacket 21. Cooling water leaves the jacket via line 25 and valves 14 and 16 are closed. For heating, valves 14 and 16 are open and valves 18 and 26 are closed.

When vessel 20 is used for beer boiling, steam introduced into the heating jacket effects boiling and vapor rich in alcohol passes from vessel 20 into stainless steel packed column 22. Water cooling is provided in the upper portion of column 22 by means of a cooling conduit 27 supplied by water through conduit 28 and valve 29. Water exits conduit 27 through pipe 30 to drain. Water cooling in packed column 22 is sufficient to cause partial condensation of vapor rising in column 22 such that a liquid condensate runs back down column 22 to vessel 20 and a second vapor rich in alcohol passes overhead through conduit 31 to a further vessel 50 having a capacity about 15–40% that of vessel 20. As shown, conduit 31 is connected to the upper region of vessel 50. However, the lower end of conduit 31 could be connected to the lower region of vessel 50 in which case fluid flowing through conduit 31 could enter vessel 20 below the surface of liquid present in vessel 50.

Vapor rising in vessel 50 passes into a further packed column 51 which contains ½ inch to 1 inch diameter porcelain marbles or packing saddles between screens 52. Column 51 extends vertically but is otherwise substantially similar to column 22. In the example discussed below, each column is stainless steel, five feet in length, and four to eight inches in diameter.

Water cooling is provided in the upper portion of column 51 by means of a cooling conduit 53 supplied by water through conduit 54 and valve 55. Water exits conduit 53 through pipe 56 to drain. Water cooling in packed column 51 is sufficient to cause partial condensation of vapor rising in column 22 such that a liquid condensate runs back down column 51 to vessel 50 and a third vapor rich in alcohol passes overhead through a conduit 57 to a total condenser 58 to which cooling water is supplied through conduit 59 and valve 50. Cooling water drains through conduit 61 and a liquid alcohol product is withdrawn through outlet 62.

If desired, water drained from any one or more of drain conduits 25, 30, 56 or 61 can be used to supply water to boiler 10. Of course, drains 25, 30, 56 and 61 would ordinarily be connected to a common drain. Similarly, water could be supplied to conduit 11 and one or more of cooling conduits 21, 27, 53, and 58 from a common source. As shown in the drawings, water flow to the cooling conduits is parallel. However, flow through one or more cooling conduits may be in series. For example, the temperature of coolant water exiting total condenser 58 is, in general, low enough to be used in cooling conduits 53 or 27 or both.

EXAMPLE

In a specific and preferred embodiment of the invention, construction of vessels 20 and 50, condenser 58, packed columns 22 and 51, and all conduits and the like which are contacted by liquid or vapor therein, are fabricated of stainless steel. Vessel 20 has a capacity of 396 gallons, and vessel 50 has a capacity of 75 gallons. Columns 22 and 51 are each five feet long and eight inches in diameter and are packed with ½ inch porcelain balls. Three hundred gallons of water are introduced into vessel 20 through conduit 70 and valve 71. Gas fired boiler 10 supplies steam to jacket 21 to heat the water in vessel 20. One half pound of ground limestone is added to vessel 120 through an access port (not shown) to ensure a source of calcium for the proper action of the alpha amylase enzyme. When the water temperature reaches about 110° F., 15 bushels of finely ground corn are added. Citric acid is added through conduit 81 from supply 82 to adjust the pH to about 6.0. When the slurry is heated to 135° F., 8 oz. alpha-amylase enzyme ("TAKATHERM") is added through conduit 83 from supply 84, the amount being according to the manufacturer's recommendation. The mash is brought nearly to a boil and an additional 200 ml of alpha-amylase enzyme is added. The mash is cooked at about 190° F. until all the starch is broken down—generally about 30 minutes. A sample port (not shown) is provided on vessel 20 to permit sampling of the mash to detect the presence of starch by the iodine test. Cooking is terminated when the test indicates the absence of starch. Agitator 24 is preferably employed during the entire mash cooking step, including preliminary heating.

Additional water is added through conduit 70 to bring the total volume of the cooked mash in vessel 20 to about 360 gallons. This addition of water will cool the cooked mash to about 155° F. and further cooling is accomplished by running cooling water through jacket 21. Two pounds of urea are added to insure a nitrogen source for the yeast. The pH is adjusted with citric acid to 4.0-4.5 and two pounds of gluco-amylase (Diazyme L-100D) are added. When the temperature reaches 85° F., the vessel is innoculated with 1.0 pounds of baker's yeast through conduit 85 from supply 86 and the system is sealed and provided with a water trap gas vent. After about 1 minute of agitation, the agitation is turned off and fermentation is allowed to continue until $CO_2$ evolution ceases, (generally about 20-48 hours). Temperature within the vessel is maintained at an appropriate temperature, depending upon the particular formulation, by the admission of cooling water and/or warm water into jacket 21 as fermentation progresses. Generally, fermentation will be carried out at a temperature of 60°-100° F., preferably, 70°-90° F. The beer thus produced has an alcoholic content of about 5-10%, 10-20 proof.

After fermentation is complete, steam is introduced to boil the beer present in vessel 20. Once equilibrium is reached and liquid alcohol product passes out of conduit 62, temperature of vessel 50 is maintained at about 180°-195° F. In this example, temperature is maintained at about 192° F. This temperature is readily maintained by the flow rate of coolant water through cooling conduit 53 or 27 or both under steady conditions of heat input to vessel 20. When distillation proceeds to the point at which it is no longer possible to maintain the temperature of vessel 50 at about 192° F., distillation is terminated. Yield is about 16-18 gallons of 192 proof alcohol and the amount of energy consumed is about 31,500 BTU per gallon of alcohol product. Distillation requires about 2.5-3 hours, cooking requires about 3-6 hours, and fermentation requires about 20-36 hours. Average total time is 38 hours. Thus, yearly yield of ethanol from a plant of this size on an around-the-clock basis is over 4000 gallons of 192 proof alcohol. A practical yield is thus about 2500 gallons per year.

Various types of fermentable materials can be used in the process such as corn, wheat, milo, and the like. It is preferred that the product has a proof of at least 190 and more preferably 192. The pH for mash cooking is preferably about 5.5 to 6.8 and for fermentation is preferably about 3.0 to 5.0. It will be apparent from the foregoing description that no external heat needs to be applied to vessel 20 (or to columns 22 and 51). The absence of an external heat source for vessel 50 is preferred to minimize energy requirements.

When fermentation is complete, the contents of vessel 20 are removed through a discharge port 72. The solid residue contains about 28% protein and can be used as an animal feed. Some or all of the dregs in vessel 50, containing about 70% alcohol, are preferably recycled to vessel 20 through conduit 73 to increase overall yield.

Temperature is readily monitored by thermometers inserted at appropriate locations in the apparatus. A thermometer 62 measures vapor temperature at the top of column 51 and thermometers 63 and 64 measure temperature of liquid and vapor respectively in vessel 50. Similar thermometers 32, 33 and 34 are located in these locations in column 22 and vessel 20. The thermometers may be of any conventional type, such as mercury thermometers, thermocouples, etc.

What is claimed is:

1. In a method of producing alcohol from fermentable material which comprises the steps of:

heating a mixture of water and a fermentable material to form a cooked mash;

fermenting the cooked mash to form a beer;

boiling the beer to produce a first vapor rich in alcohol;

partially condensing the first vapor to produce a liquid condensate and a second vapor further enriched in alcohol; and recovering an alcohol product from said second vapor;

the improvement wherein:

said steps of heating, fermenting, and boiling are carried out sequentially in a single vessel;

said liquid condensate is returned to said vessel;

said step of partially condensing said first vapor comprises passing said first vapor upwardly through a packed column and cooling the upper portion of said packed column; and said step of recovering an alcohol product from said second vapor comprises passing said second vapor from the top of said packed column to a second vessel, partially condensing vapor from the top of said second vessel to produce a further liquid condensate and a third vapor enriched in alcohol, returning said further liquid condensate to said second vessel, and condensing said third vapor to form a liquid alcohol product.

2. A method according to claim 1 wherein said liquid alcohol product is at least 190 proof.

3. A method according to claim 1 wherein said liquid alcohol product is about 192 proof.

4. A method according to claim 1 wherein said step of condensing said vapor from said second vessel comprises passing said vapor upwardly through a further packed column, and cooling the upper portion of said further packed column sufficiently to effect partial condensation.

5. A method according to claim 1 wherein heat for said heating and boiling steps is supplied by passing steam through a heat exchange conduit provided in said vessel and wherein the cooked mash is cooled for fermentation by passing water through said heat exchange conduit.

6. A method according to claim 1 wherein the mash cooking step comprises heating water, adding enzyme to the heated water, adding a fermentable grain to the heated water with agitation, and boiling the admixture for a time sufficient to form a cooked mash in which the starch in the grain is broken down.

7. A method according to claim 1 wherein the temperature of the cooked mash is reduced to a temperature not above 90° F. for fermentation.

8. A method according to claim 7 wherein pH of the mash is adjusted with citric acid prior to fermentation to a pH suitable for fermentation.

9. A method according to claim 1 wherein the temperature of said second vessel is maintained at about 160°–180° F.

10. A method according to claim 9 wherein said temperature is maintained by controlling the rate of cooling of at least one of said packed column and said further packed column.

11. A method according to claim 1 wherein no external heat is supplied to said second vessel.

12. Apparatus for producing alcohol from fermentable material comprising:

a vessel for sequentially heating a mixture of water and fermentable material to form a cooked mash, for fermenting the cooked mash to form a beer, and for boiling the beer to produce a first vapor rich in alcohol;

means for supplying fermentable material to said vessel;

means for supplying water to said vessel;

means for heating said vessel to a temperature sufficient for forming a cooked mash and for boiling beer;

means for supplying enzymes to said vessel;

means for supplying yeast to said vessel;

means for cooling said vessel to a temperature suitable for fermentation of a cooked mash;

means for partially condensing said first vapor to produce a liquid condensate and a second vapor further enriched in alcohol, said partial condenser means comprising a packed column extending generally upwardly and having its lower end mounted to the top of said vessel and in fluid communication therewith whereby said first vapor passes upwardly therethrough, and means for cooling the upper end of said packed column;

means for returning said liquid condensate to said vessel; and means for recovering an alcohol product from said second vapor, said alcohol product recovery means comprising a second vessel, means for passing vapor from the top of said packed column to said second vessel, means for partially condensing vapor passing from the top of said second vessel to produce a further liquid condensate and a third vapor enriched in alcohol, means for returning said further liquid condensate to said second vessel, and means for condensing said third vapor to form a liquid alcohol product.

13. Apparatus according to claim 12 wherein said packed column is inclined upwardly at an angle of from 35° to 65° to the horizontal.

14. Apparatus according to claim 12 wherein said means for partially condensing vapor passing from the top of said second vessel comprises a further packed column extending generally upwardly and having its lower end mounted to the top of said second vessel and in fluid communication therewith whereby said vapor passes upwardly therethrough, and means for cooling the upper portion of said further packed column.

15. Apparatus according to claim 14 wherein said packed column is substantially vertical.

16. Apparatus according to claim 12 wherein said vessel heating means and vessel cooling means comprise a heat exchange conduit in said vessel, and means for alternately supplying steam or water to said heat exchange conduit.

17. Apparatus according to claim 12 further comprising means for agitating the contents of said vessel.

18. Apparatus means according to claim 12 wherein said second vessel is free of external heating means.

19. Apparatus according to claim 16 further comprising boiler means for raising steam, and means for supplying steam to said heat exchange conduit.

20. Apparatus according to claim 12 wherein said means for passing vapor from the top of said packed column to said second vessel comprises a conduit having one end in fluid communication with the upper end of said packed column and having its other end in fluid communication with the upper portion of said second vessel.

* * * * *